United States Patent
Thoerner et al.

(10) Patent No.: US 8,673,879 B2
(45) Date of Patent: Mar. 18, 2014

(54) SKIN PROTECTANT, PARTICULARLY AGAINST HYDROPHOBIC (LIPOPHILIC) AND AGAINST HYDROPHILIC (LIPOPHOBIC) HARMFUL SUBSTANCES

(75) Inventors: Brigitte Thoerner, Duesseldorf (DE); Petra Allef, Essen (DE); Christian Schmidt, Hamburg (DE); Marcel Veeger, Goch (DE); Stefani Schmidt, Hamburg (DE); Tanja Kloeren, Krefeld (DE); Anne Claassen, Kempen (DE)

(73) Assignee: Evonik Degussa GmbH, Essen (DE)

( * ) Notice: Subject to any disclaimer, the term of this patent is extended or adjusted under 35 U.S.C. 154(b) by 30 days.

(21) Appl. No.: 13/379,489

(22) PCT Filed: Jun. 30, 2010

(86) PCT No.: PCT/EP2010/059244
§ 371 (c)(1),
(2), (4) Date: Dec. 20, 2011

(87) PCT Pub. No.: WO2011/012394
PCT Pub. Date: Feb. 3, 2011

(65) Prior Publication Data
US 2012/0101060 A1   Apr. 26, 2012

(30) Foreign Application Priority Data
Jul. 31, 2009  (DE) .......................... 10 2009 028 143

(51) Int. Cl.
*A61K 31/715*   (2006.01)

(52) U.S. Cl.
USPC .......................................................... 514/54

(58) Field of Classification Search
USPC .......................................................... 514/54
See application file for complete search history.

(56) References Cited

U.S. PATENT DOCUMENTS

| | | | |
|---|---|---|---|
| 4,900,550 A | 2/1990 | Lowry | |
| 6,376,438 B1 | 4/2002 | Rosenberger et al. | |
| 6,471,983 B1 | 10/2002 | Veeger et al. | |
| 6,489,275 B1 | 12/2002 | Veeger et al. | |
| 7,163,916 B2 | 1/2007 | Allef et al. | |
| 7,241,452 B2 | 7/2007 | Veeger et al. | |
| 7,297,675 B2 | 11/2007 | Allef et al. | |
| 7,670,615 B2 | 3/2010 | Veeger et al. | |
| 7,847,123 B2 | 12/2010 | Wenk et al. | |
| 7,851,511 B2 | 12/2010 | Allef et al. | |
| 7,906,664 B2 | 3/2011 | Allef et al. | |
| 7,910,119 B2 | 3/2011 | Allef et al. | |
| 2004/0170592 A1 | 9/2004 | Veeger et al. | |
| 2006/0198859 A1 | 9/2006 | Allef et al. | |
| 2007/0041927 A1 | 2/2007 | Blaeser et al. | |
| 2007/0092470 A1 | 4/2007 | Allef et al. | |
| 2008/0113895 A1* | 5/2008 | Tamareselvy et al. | 510/476 |
| 2008/0305056 A1 | 12/2008 | Jenni et al. | |
| 2009/0054521 A1 | 2/2009 | Herrwerth et al. | |
| 2009/0318570 A1 | 12/2009 | Veeger et al. | |
| 2010/0069505 A1 | 3/2010 | Veeger et al. | |
| 2010/0210499 A1 | 8/2010 | Allef et al. | |
| 2011/0021398 A1 | 1/2011 | Allef et al. | |

FOREIGN PATENT DOCUMENTS

| WO | 01 70271 | 9/2001 |
|---|---|---|
| WO | 2005 016364 | 2/2005 |

OTHER PUBLICATIONS

"Travabon und Travabon S," Stockhausen, p. 1-2, (Jan. 2005).
"Ligana Oleo-tec," Greven Hautschutz, p. 2, (Jun. 10, 2008).
"Ligana Multi-tec," Greven Hautschutz, p. 2, (Jun. 10, 2008).
Kresken, J., "Hautschutz am Arbeitsplatz," Skin Care Forum, pp. 1-8, (Oct. 1999).
International Search Report Issued Aug. 19, 2010 in PCT/EP10/59244 Filed Jun. 30, 2010.

* cited by examiner

*Primary Examiner* — Wu-Cheng Winston Shen
*Assistant Examiner* — Yih-Horng Shiao
(74) *Attorney, Agent, or Firm* — Oblon, Spivak McClelland, Maier & Neustadt, L.L.P.

(57) ABSTRACT

The invention relates to a skin protectant, particularly against hydrophobic (lipophilic) and hydrophilic (lipophobic) harmful substances, obtainable by means of an amount of at least one barrier-forming component, particularly against hydrophobic (lipophilic) harmful substances, wherein the nephelometric turbidity unit of the barrier-forming component is determined by means of turbidimetry and at least one barrier-forming component, a 1% solution in water thereof having a nephelometric turbidity unit of greater than 40 (NTU), is used to produce the protectant and a method for producing skin protectants, particularly against hydrophobic (lipophilic) and hydrophilic (lipophobic) harmful substances, where in the barrier-forming component is selected for production of the protectant such that the nephelometric turbidity unit of the barrier-forming component of the skin protectant is determined by means of turbidimetry and at least one barrier-forming component, a 1% solution in water thereof having a nephelometric turbidity unit of greater than 40 (NTU), is used to produce the skin protectant.

19 Claims, 3 Drawing Sheets

SKIN PROTECTANT, PARTICULARLY AGAINST HYDROPHOBIC (LIPOPHILIC) AND AGAINST HYDROPHILIC (LIPOPHOBIC) HARMFUL SUBSTANCES

CROSS REFERENCE TO RELATED APPLICATIONS

This application is a 35 U.S.C. §371 national stage patent application of international patent application PCT/EP10/059244, filed Jun. 30, 2010, and claims priority to German Patent Application No. 10 2009 028 143.6, filed Jul. 31, 2009.

The invention relates to a skin protectant, particularly against oily (hydrophobic) harmful substances, which can also be used in the event of a change in stress, i.e. in the case of stress from both hydrophilic and hydrophobic harmful substances and in the case of severe soiling.

With a surface area of about 1.5 to 2.0 $m^2$, the human skin is the human organ of largest surface area which perceives functions vital to the body. For this purpose, the skin contains blood vessels and lymph vessels, through the walls of which the exchange of lymph fluid, gases, nutrients and waste materials can take place in order, for example, to ensure nutrition and metabolism. Further functions of the skin are the regulation of body temperature, protection of the body against drying out and against external mechanical, chemical and bacterial effects. Thus, the secretions from sebaceous glands in the skin keep the skin supple and help in regulating the water balance in the skin. Moreover, via free nerve endings, the skin conveys inter alia touch, heat and cold and pain sensations to the organism and thus has the function of a sensory organ.

The manifold products supplied for hygiene, body care and cosmetics, such as, for example, skin cleansing products, skin protection products and skincare products, therefore serve not only primarily for the cleaning, protection or care, respectively, of the skin, but they also maintain the quality of life and ensure a person's wellbeing.

Being the body sheath, the human skin represents the connection, but simultaneously also the boundary of the human body with its outside world. In particular, contact with everything which the human organism requires for life—but also that which can harm it—takes place via it.

Particularly in the workplace, the skin can be exposed to a large number of working substances of very different types and even working substances which are generally not perceived as harmful substances can lead to skin damage in the event of long-term contact, such as e.g. skin dryness, rough cracked skin with disturbed barrier effect and/or increased risk of allergy. As well as such long-term effects of even weakly irritating substances and also the variety of working substances used in the workplace, skin protectants have to take into consideration the fact that the human skin reacts differently to external environmental influences from person to person and, as a result of this, considerable differences in the skin reaction to these influences are observed from person to person.

Skin protectants can be divided into the following categories depending on their fields of use (cf. Dr. Jens Burfeindt, Dr. Dirk Mehlan, Dr. Wolfgang Röcher in "sicher ist sicher"-Arbeitsschutz aktuell, 12 (2006), 547-551):
Protection against working substances
Facilitation of skin cleaning
Protection against swelling and softening of horny skin when working under wet conditions
Protection against UV rays Further requirements which are placed on modern skin protectants are in particular that the grip of the hands is adversely affected as little as possible and it must be ensured that the skin protectants used are compatible with the respective working materials and/or working processes, as occur for example in the automobile industry and coatings industry, and also the rubber-processing industry, i.e. they must be e.g. silicone-free, grease-free, low-grease etc.:

Thus, for example, it is a particular disadvantage of skin protection preparations which comprise silicones as ingredients that these preparations can leave behind residues on objects, e.g. on tools and/or workpieces, if such workpieces are passed by hand to a further operation. Consequently, in the case of workpieces to be painted, the workforce is unable to use such silicone-containing skin protectants. This is because these extremely difficult-to-remove silicone residues are extremely bothersome in the further processing of these workpieces, such as, for example, painting or vulcanization, and lead to painting defects, such as, for example, paint wetting disturbances and/or crater formation on the workpieces. Consequently, particularly in the automobile industry and coatings industry and also the rubber-processing industry, it is not possible to use silicone-containing skin protection products despite their excellent protective effect and acceptance by the user.

Moreover, skin protectants must be free from known penetration-promoting ingredients such as e.g. urea.

Furthermore, for ecological reasons, modern skin protectants must also be free from fluorine-containing surfactants. Skin protectants comprising such fluorine surfactants are not only ecologically unacceptable, but can likewise—as in the case of the silicone-containing skin protectants described above—lead to painting defects during the further processing of workpieces if corresponding skin protection preparation residues are found on the workpieces to be painted.

According to the invention, the effect of a skin protectant is based on an interaction of physical and physiological effects of the individual ingredients in the overall formulation. In particular, use is made of the general rule known since time immemorial "Similia similibus solvuntur" ("like is dissolved by like"), and e.g. in the case of hydrophilic (lipophobic) substances, a skin protectant is used which has an opposite profile of properties, i.e. is hydrophobic (lipophilic). Moreover, pigments or film-forming substances can delay the diffusion of a working substance into the skin and thus reduce the danger of a harmful effect for the skin.

Particularly advantageous skin protectants to be mentioned are also those compositions which, besides their protective effect against harmful substances, also reduce the adhesion of strongly adhering soilings such as e.g. water-insoluble soilings due to oils, paints, graphite, metal dusts, adhesives, synthetic resins etc., or themselves exert a cleaning effect as a result of special ingredients. As a result of this, the subsequent skin cleaning can be carried out significantly more quickly and more gently, which naturally has a positive effect on the condition of the skin. Such particularly advantageous skin protectants are available from Evonik Stockhausen GmbH, Krefeld under the trade name TRAVABON®.

Skin protectants are supposed to protect the human skin against the very wide variety of hazards in the outside world, such as, for example, effects of the weather, water and aqueous solutions, chemicals, and also soilings of any type. Usually, such skin protectants in anhydrous form cover the human skin with a "barrier" or protective film which cannot be absorbed by the skin. Ideally, this protective film is applied to the skin in such a way that its presence is not noticeable by those in the vicinity since it is invisible to them and/or cannot be felt by the user on his or her skin. Nevertheless, most of the commercially available products comprise large amounts—for example up to 25% by weight—of absorbable, well-covering, and also well-adhering to the skin, nontoxic inorganic solids in pigment form. By way of example, mention may be made here of oxides, such as e.g. zinc dioxide and titanium dioxide, the alkaline earth metal carbonates and hydrogencarbonates, and also sulfates, in particular their magnesium, calcium and strontium salts. Furthermore, as well as silicon dioxide and silica gels, mention is also to be made of mineral silicates such as e.g. aluminum silicates, magnesium-aluminum silicates, bentonite, kaolins and talc. Such inorganic pigments act as barrier agent in that they form a physical protective layer on the skin. Such inorganic barrier agents such as e.g. kaolin or talc, however, give the user a very unpleasant dry skin feel. In the event of high heat and/or if the user sweats or wears gloves, the skin feels "sticky". This significantly reduces the acceptance by the user with regard to the use of such skin protectants in the workplace.

Moreover, skin protectants are supplied commercially which are supposed to offer protection both against hydrophilic (lipophobic) and also against hydrophobic (lipophilic) harmful substances in order to be able to facilitate a certain protection for the skin even in the event of frequently changing stress. Nevertheless, such ambivalent skin protectants are often limited in their effectiveness compared to skin protectants whose use spectrum is limited merely either exclusively to hydrophilic (lipophobic) or exclusively to hydrophobic (lipophilic) harmful substances.

Further commercially available skin protectants are compositions with astringent properties which, by virtue of the use of special tanning substances as ingredients, utilize their astringent effect in such a way that the uppermost cells of the horny layer become strengthened. This achieves an increase in the mechanical stressability and the barrier effect of the skin. This results in the suitability of such skin protectants both in the event of increased stressing of the skin due to mechanical effects, and also in the event of frequently changing skin stress due to aqueous and oily substances.

As already stated previously, the skin can be exposed to a large number of working substances of very different types in the workplace, with even working substances which generally are not considered hazardous substances having the potential to lead to skin damage in the event of long-term effect. However, it has been found that, with regard to the entire spectrum of conceivable working substances and the diverse fields of use of skin protectants resulting therefrom in the workplace, there is precisely an evergrowing need for a skin protectant which offers in particular an improved protective effect for the skin, even in the case of frequently changing stress, i.e. protection both against hydrophilic (lipophobic) and also against hydrophobic (lipophilic) harmful substances, and displays a comparable cleaning effect and/or a comparable protection against skin soilings upon application.

Nevertheless, these skin protectants should give the user an improved—that is to say "a more pleasant"—skin feel than the commercially available skin protection products with physical barrier agents, such as e.g. kaolin, talc, etc.

In order to offer protection against soiling, that is to say to ensure simplified cleaning, surfactants are then added to the products. However, most surfactants increase the penetration of the harmful substances, meaning that to date no skin protectant is available on the market which offers protection against oily and aqueous noxae and protection against soiling.

It was therefore an object to provide a skin protectant which, even in the case of frequently changing harmful substance stress, in particular due to hydrophobic (lipophilic) and also hydrophilic (lipophobic) harmful substances, has a cleaning effect which is preferably at least comparable to that of skin protectants known in the prior art, and also, upon use, preferably brings about a "pleasant" skin feel, and which is preferably fluorine surfactant-free and silicone-free, and also a corresponding production method of such a skin protectant.

The object according to the invention was achieved by a skin protectant, in particular against is hydrophobic (lipophilic) and also against hydrophilic (lipophobic) harmful substances, which is obtainable by a fraction of at least one barrier-forming component, where the nephelometric turbidity value of the barrier-forming component is determined by means of turbidimetry and the barrier-forming component, the 1% strength solution of which in water has a nephelometric turbidity value greater than 40 (NTU), which is used for producing the composition.

It was entirely surprising that hydrophobic polymers, i.e. polymers which dissolve in water to give only cloudy solutions, with a nephelometric turbidity value greater than 40, as barrier-forming component in skin protectants offer good protection against oily noxae. Moreover, the skin protectant according to the invention protects not only against oily, hydrophobic (lipophilic) harmful substances, but also in the event of a change in stress, i.e. in the event of stress from both hydrophilic and also hydrophobic harmful substances and in the case of severe soiling. By contrast, it was to be expected that hydrophobic polymers as barrier-forming components in skin protectants protect exclusively against hydrophilic (lipophobic) harmful substances, i.e. against aqueous noxae. The fact that these in the skin protectants according to the invention likewise also protect against hydrophobic (lipophilic) harmful substances, in particular oily noxae, was completely unexpected.

The present invention therefore provides skin protectants as described in the claims and hereinbelow, the use thereof as protectants against hydrophilic (lipophobic) harmful substances and as protectants both against hydrophobic (lipophilic) and also against hydrophilic (lipophobic) harmful substances and optionally for facilitating skin cleaning following soiling, and also a method for producing corresponding skin protectants.

The skin protectants according to the invention have the advantage that, even without the presence of silicone or fluorine surfactants, they offer good protection against lipophilic noxae. By dispensing with said surfactants, the known disadvantages of the inadvertent transfer of the lipophilicity or hydrophobicity to touched workpieces are avoided.

Moreover, the skin protectants according to the invention have the advantage that their use can offer not only good protection against lipophilic noxae, but also against hydrophilic noxae. The skin protectants according to the invention therefore offer particularly good protection during activities in which both contact with lipophilic and also with hydrophilic noxae can occur.

The skin protectants according to the invention and the use thereof, and also a method for producing them are described below by way of example without any intention of limiting the invention to these exemplary embodiments. Where ranges, general formulae or compound classes are given below, then these are intended to include not only the corresponding ranges or groups of compounds that are explicitly mentioned, but also all part ranges and part groups of compounds which can be obtained by removing individual values (ranges) or compounds. Where documents are cited within the scope of the present invention, then their content, especially with regard to facts to which reference is made, is deemed, in its entirety, to form part of the disclosure of the present invention. Unless stated otherwise, data in percent are always percent by mass or percent by weight. Where average values are given below, then, unless stated otherwise, these are the number-average values. Where solutions of polymers in water are discussed in the course of the present invention, then these are to be understood as also meaning those solutions, dispersions and/or suspensions in which parts of the polymers are present in dissolved form and parts of the polymers are present in undissolved or swollen form.

The skin protectant according to the invention, in particular against hydrophobic (lipophilic) harmful substances, is characterized in that it comprises at least one barrier-forming component, where a 1% strength by weight solution of this barrier-forming component in water has a nephelometric turbidity value, determined by means of turbidimetry, greater than 40 (NTU), preferably greater than 50 and particularly preferably greater than 60.

The nephemological turbidity value can be determined e.g. using a turbidimeter of the type HACH Turbidimeter 2100P ISO from Hach Company, Loveland, Colo. (USA) using round cuvettes with screw closure from Hach Company, Loveland, Colo. (USA), catalog number 24347-06 and using the calibration substances StablCal Solution HACH (<0.1 NTU), catalog number 26597-42, StablCal Solution HACH (20 NTU), catalog number 26601-42, StablCal Solution HACH (100 NTU), catalog number 26602-42 and StablCal Solution HACH (800 NTU), catalog number 26605-42, all likewise from Hach Company.

The fraction of barrier-forming components, the 1% strength by weight solution of which in to water has a nephelometric turbidity value as stated above, in the overall composition of the skin protectant according to the invention (NTU) is preferably from 0.01 to 5% by weight, preferably from 0.03 to 5% by weight and particularly preferably from 0.03 to 3% by weight.

In the skin protectant according to the invention, it is possible to use any barrier-forming component that can be used in cosmetic formulations and whose 1% strength by weight solution in water has a nephelometric turbidity value in the ranges stated above.

Preferably, one or more naturally occurring and/or synthetically produced, preferably naturally occurring, polymers, the 1% strength by weight solution of which in water have a nephelometric turbidity value in the ranges stated above, are present as barrier-forming component in the skin protectant according to the invention.

Polymers which can be used as barrier-forming components, whose 1% strength by weight solution in water have a nephelometric turbidity value in the ranges given above, and that are present in the skin protectants according to the invention are particularly preferably polysaccharides, which can be selected particularly advantageously from the group of gums. The gums include e.g. plant or tree saps which harden in the air and form resins or extracts from aquatic plants. From this group, according to the invention, it is possible to select in particular gum arabic, carob seed flour, tragacanth, karaya, guar gum, pectin, gellan gum, carrageenan, agar, algins, *chondrus*, xanthan gum etc. or mixtures thereof.

Further particularly preferred polysaccharides are in particular alginates, i.e. salts and esters of alginic acid, preferably sodium alginate or *Chondrus crispus* (carrageenan), and also the plant gum known under the INCI name Biosaccharide Gum-4.

Polymers which can be used as barrier-forming components whose 1% strength solution in water have a nephelometric turbidity value in the ranges given above, are also preferably polyurethanes and polyacrylates.

In order to ensure that the skin protectants according to the invention offer protection against skin soilings and also exhibit a cleaning effect which is comparable with that of the skin protection products known in the prior art, it may be advantageous if the skin protectants according to the invention comprise at least one surfactant.

In principle, all surfactants, in particular surfactants suitable for use in cosmetic compositions, can be used in the skin protectants according to the invention. In this connection, it should be taken into consideration that surfactants can per se represent noxae for the human skin and/or some surfactants can, moreover, be penetration-promoting, meaning that this runs counter to the effect desired for a skin protectant, namely to specifically prevent the pentration of harmful substances into the skin.

Consequently, in the skin protectants according to the invention, preference is given to using only those surfactants for which it is ensured that the protective effect of the composition as a whole is not thereby adversely affected. Furthermore, the surfactants which can be used should have good skin compatibility, especially also because skin protectants are "leave on" products and the composition is intended to remain on the skin of the user over a prolonged period.

Particularly preferred surfactants are therefore mild or skin-compatible surfactants which may be present on their own or in combination in the skin protectants according to the invention.

Such surfactants are, for example, amino acid surfactants, in particular acylamino acids and salts thereof, such as acyl glutamates, for example sodium acyl glutamate, di-TEA palmitoyl aspartate and sodium caprylic/capric glutamate, acyl peptides, for example palmitoyl hydrolyzed milk protein, sodium cocoyl hydrolyzed soya protein and sodium/potassium cocoyl hydrolyzed collagen, sarcosinates, for example myristoyl sarcosine, TEA lauroyl sarcosinate, sodium lauroyl sarcosinate and sodium cocoyl sarcosinate, acyl taurides, for example sodium lauroyl taurate and sodium methyl cocoyl taurate, isethionates, in particular acyl isethionates having 8 to 24 carbon atoms, e.g. sodium/ammonium cocoyl isethionate, sulfosuccinates, for example dioctyl sodium sulfosuccinate, disodium laureth sulfosuccinate, disodium lauroyl sulfosuccinate and disodium undecylenamido MEA sulfosuccinate.

Further mild surfactants which can be used are zwitterionic surfactants, in particular the so-called betaines, such as e.g. the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and also cocoacyl aminoethylhydroxyethyl carboxymethylglycinate. A particularly preferred zwitterionic surfactant is the fatty acid amide derivative known under the INCI name Cocamidopropyl Betaine.

Surfactants which can preferably be used according to the invention are amphoteric surfactants, in particular acyl-/dialkylethylenediamine, for example sodium acyl amphoacetate, disodium acyl amphodipropionate, disodium alkyl amphodiacetate, sodium acyl amphohydroxypropyl sulfonate, disodium acyl amphodiacetate and sodium acyl amphopropionate, N-alkylamino acids, for example aminopropylalkylglutamide, alkylaminopropionic acid, sodium alkyl imidodipropionate and lauroamphocarboxyglycinate, N-alkyl- or N-alkenylbetaines having at least 8 carbon atoms, such as e.g. lauramidopropyl-betaine and oleylamidopropylbetaine.

Surfactants which can be used particularly preferably according to the invention are polyethylene and polypropylene glycol derivatives, in particular polypropylene glycol ethers which preferably have at least 6 carbon atoms, such as, for example, laureth-6 or oleth-5.

Very particularly preferred surfactants, of which preferably at least one is present in the skin protectants according to the invention, are preferably selected from the group comprising: sodium stearoyl glutamate, sodium cocoamphoacetate, disodium cocoyl glutamate, sodium cocoamphopropionate, dioctyl sodium sulfosuccinate, and sodium lauroyl sarcosinate.

The skin protectants according to the invention preferably comprise from 1 to 12% by weight, preferably 1 to 10% by weight and very particularly preferably 1 to 8% by weight, of active substance, based on the total composition of the skin protectant, of at least one, preferably mild surfactant, preferably selected from the surfactants specified above.

In the skin protectants according to the invention, polyols and derivatives thereof, in particular from 0.1 to 5% by weight, preferably from 1 to 5% by weight and very particularly preferably from 2 to 4% by weight, based on the total composition of the skin protectant, can be present e.g. as moisturizers. It was surprising that propylene glycol, which is known to promote penetration, displays no negative properties on the protective effect.

According to the invention, polyols, which can be used on their own or as a mixture with one or more other polyols, are understood as meaning all compounds which fall under the definition given in Römpp's Lexikon der Chemie, Version 3.4 Römpp Online, Georg Thieme Verlag. In particular, customary polyalcohols and/or polyhydroxy compounds, preferably having 2 to 15 carbon atoms and at least two hydroxyl groups, which are suitable, i.e. physiologically compatible, for cosmetic and/or pharmaceutical formulations are suitable. By way of example, mention may be made here of polyhydric alcohols such as straight-chain, branched or cyclic alkanols having 2 to 15, preferably 2 to 6, carbon atoms, with glycerol and/or 1,2-propanediol being particularly preferred. Moreover, glycols, such as e.g. polyethylene glycols, polypropylene glycols, but also sugars and sugar derivatives, preferably fructose, glucose, sucrose, sugar alcohols, in particular sorbitol, mannitol etc., may be present in the skin protectants according to the invention. The polyols or polyol derivatives preferably have free OH groups and are therefore preferably not compounds whose OH groups are etherified.

Moreover, the skin protectant according to the invention preferably has water as a component. Preferably, the fraction of water in the overall composition is from 50 to 90% by weight, based on the total composition of the skin protectant.

As further components, the skin protectants according to the invention can optionally comprise auxiliaries, additives and/or active ingredients, such as e.g. dyes, solubilizers, complexing agents, tanning substances, pigments, sequestrants, photoprotective filters or perfumes and fragrances, pH regulators, stabilizers, preservatives, for example parabens, i.e. p-hydroxybenzoic acid alkyl esters, such as e.g. methyl, ethyl, propyl and/or butyl paraben, and also phenoxyethanol etc., antioxidants and/or oily or aqueous care components as further components. Preferably, the fraction of these further components is in the amounts customary for cosmetic and/or pharmaceutical formulations. Preferably, the fraction of the further components is from 0.01 to 25% by weight, preferably 0.05 to 10% by weight, based on the total weight of the skin protectant, where the person skilled in the art selects the weight fraction of these components such that it does not result in any impairment of the barrier formation of the skin protectants according to the invention on account of possible penetration-promoting properties of these auxiliaries, additives and/or active ingredients.

Although the skin protectants according to the invention display an excellent protective effect in the case of stress from both hydrophilic and also hydrophobic harmful substances and in the event of severe soiling, without comprising fractions of the inorganic pigments usually used in skin protectants, such as, for example, oxides, e.g. zinc dioxide and titanium dioxide, alkaline earth metal carbonates and hydrogencarbonates and also sulfates, in particular their magnesium, calcium and strontium salts, and also silicon dioxide and silica gels, mineral silicates such as e.g. aluminum silicates, magnesium-aluminum silicates, bentonites, kaolins and in particular talc, the skin protectants according to the invention can comprise up to 10% by weight, based on the total weight of the skin protectant, of inorganic pigments, in particular selected from the aforementioned inorganic pigments as additives, in order, for example, to improve the skin feel or to introduce a sun protection factor.

By adding synthetic and/or natural tanning substances, preferably from 0.1 to 5% by weight, preferably 0.5 to 2% by weight and particularly preferably 0.5 to 1.5% by weight, based on the total composition of the skin protectant, as further component in the skin protectants according to the invention, it is possible to achieve an improvement in the skin barrier, in particular also in the case of already predamaged skin, as a result of which effective assistance in skin regeneration is effected. As synthetic or natural tanning substances, all known tanning substances which are suitable for cosmetic applications may be present in the skin protectant. Preferably, the synthetic tanning substances are those selected from the groups comprising synthanes, e.g. phenolsulfonic acid-phenol-urea-methanal condensates, sodium salts of phenolsulfonic acid-formaldehyde polycondensates (TAMOL PP—manufacturer BASF AG, Ludwigshafen, or those under the trade name Eucoriol®—INCI name: "Sodium Bischlorophenyl Sulfamine" (manufacturer: Evonik Stockhausen GmbH, Krefeld). Natural tanning substances are e.g. tannins or spray-dried hamamelis extracts etc., where an addition in an amount of from 0.1 to 5% by weight, based on the total amount of the skin protectant, of Hamamelis virginiana as a natural tanning substance is particularly preferred.

The skin protectants according to the invention are preferably silicone-free and/or advantageously also have no ecologically unacceptable fluorine surfactants as ingredients. It is thus ensured that, during the further processing of workpieces, no painting defects arise if skin protection preparation residues were to be found on the workpieces to be painted. Consequently, the compositions according to the invention can be used particularly advantageously especially in the automobile industry and the coatings industry and also the rubber-processing industry, in contrast to silicone-containing and fluorine surfactant-containing skin protection products.

According to the invention, preference is given in particular to skin protectants which comprise a.) from 1 to 12% by weight of at least one surfactant, b.) from 0.1 to 5% by weight of at least one polyol and/or polyol derivative, c.) 0 to 25% by weight, preferably 1 to 5% by weight, of cosmetic and/or pharmaceutical auxiliaries, additives and/or active ingredients, d.) 0.01 to 5% by weight of at least one barrier-forming component, the 1% strength by weight solution of which in water has a nephelometric turbidity value greater than 40 (NTU), and e.) water, with the proviso that the amounts of components a) to e.) add up to 100% by weight. These skin protectants are particularly preferably silicone-free and fluorine surfactant-free, absorb readily into the skin and/or preferably and form no detectable film on the skin.

Very particularly preferred skin protectants according to the invention are e.g. the skin protectants listed in the examples described below, in particular those which can be found in tables 1 to 4.

The skin protectants according to the invention can be used as protectants against hydrophilic (lipophobic) harmful substances and advantageously even as protectants both against hydrophobic (lipophilic) and also against hydrophilic (lipophobic) harmful substances. Moreover, the use of the skin protectant according to the invention can facilitate skin cleaning.

The invention relates, moreover, to a method for producing skin protectants, in particular against hydrophobic (lipophilic) harmful substances, where a barrier-forming component for producing the composition is selected in such a way that the nephelometric turbidity value of the barrier-forming component of the skin protectant is determined by means of turbidimetry, and at least one barrier-forming component, the 1% strength by weight solution of which in water has a nephelometric turbidity value greater than 40 (NTU), is used to produce the skin protectant.

According to the invention, preference is given to a method in which, in each case based on the total composition of the skin protectant, a.) from 1 to 12% by weight of at least one surfactant, b.) from 0.1 to 5% by weight of at least one polyol and/or polyol derivative, c.) 0 to 25% by weight, preferably 1 to 5% by weight of cosmetic and/or pharmaceutical auxiliaries, additives and/or active ingredients, d.) 0.01 to 5% by weight of at least one barrier-forming component, the 1% strength by weight solution of which in water has a nephelometric turbidity value greater than 40 (NTU), and e.) water, where the amounts of the components a) to e.) add up to 100% by weight, are used to produce the skin protectant.

It is advantageous that, as a result of the method according to the invention, skin protectants are available whose property profile and/or protection profile could hitherto not be attained, namely the guarantee of a protective effect both against oily and aqueous noxae with simultaneous protection against soiling, i.e. also the adhesion of strongly adhering soilings such as e.g. water-insoluble soilings due to oils, paints, graphite, metal dusts, adhesives, synthetic resins etc. can be reduced by the skin protectants according to the invention. As a result of this, it is particularly advantageous that a subsequent skin cleaning can be carried out significantly more quickly and more gently.

It is also advantageous that, for the skin protectants according to the invention, no inorganic barrier agents or inorganic pigments such as e.g. kaolin or talc are required which can give the user a very unpleasant dry skin feel in the event of heat or when wearing gloves, as a result of which the acceptance by the user with regard to the use of skin protectants in the workplace is significantly improved.

The present invention is illustrated in more detail by reference to FIGS. 1 to 7, without being limited thereto.

Hereinbelow, the invention is described by reference to examples and investigations, in particular the skin compatibility test with the help of the Duhring chamber test, test into disruption of the skin barrier with the help of the Tewameter and test of the cleaning power with the help of the handwashing test and ex vivo methods such as e.g. the 3D skin model etc., and also figures in the form of diagrams.

These explanations are merely by way of example and do not limit the invention present here. Unless stated otherwise, the stated quantitative amounts, fractions and percentages are based on the weight and the total amount or on the total weight of the skin protectants according to the invention.

EXAMPLES

Test Methods

I. Determination of the Nephelometric Turbidity Value (NTU Value)

1. Field of Application:

Measurement of the turbidity (undissolved constituents) in aqueous media.

2. Short Description of the Method:

Nephelometry is an optical analytical method for determining the fractoin of solids in suspensions, aerosols and/or turbid dispersions etc. The turbidity measurement here is based on the Faraday-Tyndall effect, in which the intensity of the scattered light is measured.

Using the turbidimeter used according to the invention, the turbidity was determined by measuring the decrease in the intensity of the light through the scattering medium (turbidimetry).

3. Instruments:

HACH Turbidimeter 2100P ISO from Hach Company, Loveland, Colo. (USA)

Water processing instrument ELGA PURELAB Classic from ELGA Labwater, Celle (Germany).

round cuvettes with screwtop closure Hach Cat. 24347-06 heatable magnetic stirrer general laboratory equipment

4. Chemicals:

| Ultrapure water | | |
|---|---|---|
| StablCal Solution HACH | <0.1 NTU | Cat. 26597-42 |
| StablCal Solution HACH | 20 NTU | Cat. 26601-42 |

-continued

| Ultrapure water | | |
|---|---|---|
| StablCal Solution HACH | 100 NTU | Cat. 26602-42 |
| StablCal Solution HACH | 800 NTU | Cat. 26605-42 |

5. Calibration

The calibration was carried out using carrageenan (Viscarin® PC209 from FMC Biopolymer, Philadelphia (USA)).

Figure 1:
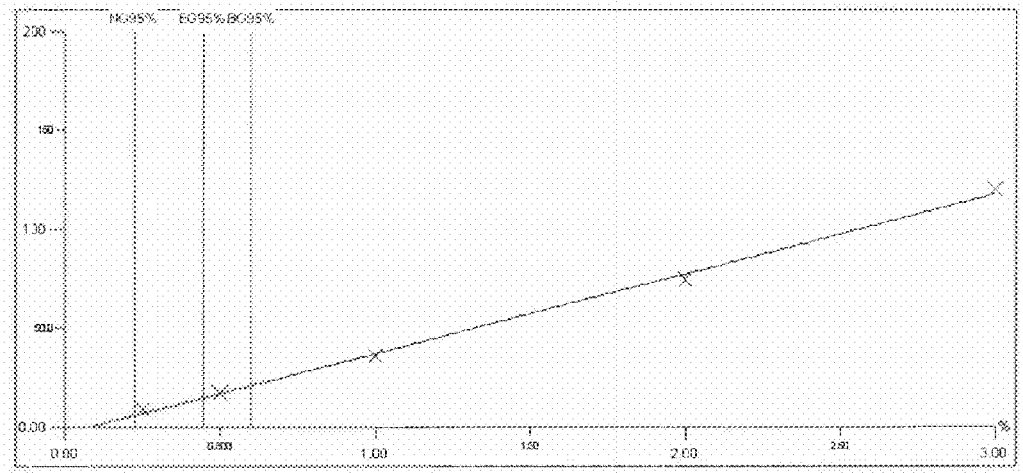
FIG. 1 shows the calibration curve for determining the nephelometric turbidity value (NTU value). In this, NG: detection limit, EG: capture limit and BG: determination limit.

The calibration curve is shown in FIG. 1. The calibration is calculated in accordance with DIN 38402 Part 51:

| Results for function: Y = 40.25x − 2.92 | N = 5 measurement values |
|---|---|
| Correlation coefficient r | 0.999 |
| Residual standard deviation sy | 2.427 |
| Method deviation sx0 | 0.060 |
| Rel. method standard deviation Vx0 | 4.467 |

Calibration of the Instrument:

The instrument was calibrated in accordance with the details and instructions from the instrument manufacturer—Hach Company, Loveland, Colo. (USA)—using a stabilized formazin standard, which is supplied by Fach under the name StablCal® as standardized solution (see point 4 "Chemicals" and catalog numbers (cat.) given therein). Here, it was to be ensured that the measurement solutions were free from air bubbles.

6. Sample Preparation:

0.1, 1.0, 2.0 and/or 3.0 g samples (tables 6a and 6b) were made up to 100.0 g with ultrapure water and stirred for 2 h on the magnetic stirrer at 500 rpm. After a standing time of 3 hours, the sample was measured.

7. Carrying Out the Determination:

The preprepared solutions were poured, free from air bubbles, into the cuvettes provided for this purpose and measured using the turbidimeter which had been freshly calibrated beforehand. The displayed value indicated the turbidity in the form of the nephelometric turbidity value (NTU value).

II. Ex vivo Method: 3D Skin Model

3-Dimensional skin models have an analogous skin structure to the human skin. They can also be used as test models in order to investigate the barrier repair following damage with model irritants (cf. A. zur Mühlen et al, "Using skin models to assess the effects of a protection cream on skin barrier function", Skin Pharmacol. Physiol 17 (4):167-179).

In order to analyze the influence of active ingredients on the lipid content of the skin, using such a 3-dimensional skin model with a 1:1 mixture of undecylenic acid:ethyl acetate as model irritant, the condition of the skin model was characterized via the analysis of the inflammation parameters (IL-1α) and of the LDH and MTT value. Only if damage was present in in the subtoxic region, i.e. no massive cell damage is caused by the model noxae, could a regeneration of the skin barrier take place.

The skin models EST 1000 from CellSystems® Biotechnologie Vertrieb GmbH were transferred to 6-well cell culture plates with in each case 900 µl of "maintenance medium". The cultures were preincubated for 1 hour at 37° C. and 5% $CO_2$. After the preincubation phase, the activity of the lactate dehydrogenase (LDH) in the medium was determined, and the entire "maintenance medium" (900 µl) was exchanged. 30 µl 50% of a 1:1 mixture of undecylenic acid/ethyl acetate as model noxa for oily noxae in PBS (phosphate buffer) were then pipetted onto the corresponding skin model. Only PBS (PBS with Ca and Mg, available from Biochrom, Berlin, Germany) was added to the negative controls. After 40 min, the LDH activity in the medium was determined again and all of the samples were washed 3× with 500 µl of PBS. Media exchange was then again carried out. Then, in each case 30 µl of the corresponding test substance (see also plate coating) were pipetted onto the surface of the cultures.

After incubation for 24 h, the LDH activity was determined. The skin models were then subjected to an MTT test (24 and 48 h).

To test the skin protection products, the skin protectant was applied to the skin model using a sterile pad prior to application of the model noxae.

Determination of the LDH Release:

The LDH test is a customary in vitro cytotoxicity test, the principle of which is based on the determination of the enzyme activity of lactate dehydrogenase (LDH) in the cytoplasma which is released from destroyed or damaged cells and can thus be detected in vitro in the cell culture medium. Lactate dehydrogenase is a stable cytoplasmatic enzyme which is released very quickly into the cell culture medium when the cell membrane is destroyed. The LDH activity is determined by means of an enzymatic test. The following principle applies here: the greater the degree of cell damage, the greater the amount of released LDH in the medium.

The quantification of the LDH activity was carried out using a commercially available LDH test kit from Roche Diagnostics, Mannheim, Germany and was carried out in accordance with the manufacturer's instructions. When determining the activity of the LDH, an LDH dilution series (LDH, Roche Diagnostics, Mannheim, Germany) was run alongside as standard.

Determination of the Viability (Standard MTT Test):

The MTT test is a cytotoxicity test. Cells are treated invitro with the naming dye, a yellow tetrazoliumsalt, in order to measure their viability or the fraction of living cells compared to a control sample of cells.

The vitality of the cells was determined using the standard MTT test. Here, the yellow tetrazolium salt MTT (Thiazolyl Blue Tetrazolium Bromide, manufacturer: Sigma) was reduced by mitochondrial dehydrogenase of metabolically active cells in a blue formazan dye, which was then determined photometrically.

Determination of the IL-1α Content:

Interleukins (IL-x) are peptide hormones belonging to the cytokines, i.e. they are endogenous messenger substances of the cells in the immune system. Interleukin-1 is formed by macrophaqes, endothelialcells, fibroblasts and some other cells and is a signaling substance that promotes inflammation. IL1α plays an important role in maintaining the skin barrier function. The quantification of the aforementioned parameters was carried out using commercially available test kits (interleukin 1α, R&D Systems GmbH, Wiesbaden-Norderstedt, Germany) and was carried out in accordance with manufacturer's instructions.

III. Repetitive Occlusive Irritation Test: Skin Protection Products

Test areas/fields were marked on the volar forearm of subjects. The starting values of the skin were then determined by visual assessment. After this determination, the skin protection product was then applied to the forearm. A control field and a field as positive standard remained untreated or free.

After a contact time of 10 min, excess product was wiped off with a pad. Finn chambers with a 1:1 mixture of undecylenic acid/ethyl acetate as model noxa for oily noxae or 2.5% strength sodium lauryl sulfate solution (SDS) as model noxa for aqueous noxae were then placed on the test fields. One test field remained free as control field.

After 30 min in the case of tests into the protective effect of the skin protectant against oily noxae, or 60 min in the case of tests on the composition against aqueous noxae, the Finn chambers were removed and rinsed with water. On the following day, before the next test cycle, the TEWL value and the corneometer value were again determined and visually assessed. The test procedure was repeated for 4 days, then on the 5th day the measurements of the skin values were carried out (TEWL, corneometer and visual assessment).

The test on frequently changing stress of the skin was carried out as follows:

In the mornings, 2.5% strength by weight sodium lauryl sulfate solution (SDS) was applied to the skin of the subjects, and in the afternoons an ethyl acetate/undecylenic acid mixture (1:1) was applied, in each case for 30 min.

The visual assessment was made in accordance with the evaluation scheme given in table 0.

TABLE 0

Evaluation scheme for the visual assessment.

| Criteria | Symptoms | Points |
|---|---|---|
| R = reddening (Erythema) | Negative | 0 |
| | very slight, punctiform or diffuse erythema | 1 |
| | easily recognizable, strictly limited erythema | 2 |
| | medium-strength erythema | 3 |
| | severe, firey red erythema with edema or epidermal defect (blisters, necroses) | 4 |
| S = Flaking | Negative | 0 |
| | Dryness, shiny effect | 1 |
| | fine flaking | 2 |
| | moderate flaking | 3 |
| | severe flaking with peeling | 4 |
| F = Fissures (Cracks) | Negative | 0 |
| | very superficial epidermal separation | 1 |
| | one or more wide fissures | 2 |
| | deep fissures with bleeding and exudation | 3 |

If an evaluation was between two evaluation points, the assessment could be in steps of 0.5 for the purposes of further differentiation. The average was then formed from the sum of the individual irritation values of R, S and F.

V. Handwashing Test

The preliminary handwashing test was carried out with 10 subjects as follows:

1.2 g of test product were applied and rubbed in 0.5 g of soiling was rubbed into the palms of the hands and on the backs of the hands 1 ml of water was added and washed for 30 sec again 1 ml of water was added and left to wash for 30 sec rinsing was under running cold water the assessment of the cleaning effect was carried out in accordance with the 6-point scale.

As model soiling, a mixture of oil, grease and various pigments, which comprised 54.15% by weight of castrol engine oil, 18.05% by weight of vaseline, 18.05% by weight of Adeps Lanae, 3.61% by weight of graphite, 5.42% by weight of flame black and 0.72% by weight of iron oxide, was used.

The degree of residual soiling on the palms of the hands and on the backs of the hands was evaluated after the washing according to the following 6-point scale.

0=clean

1=slight residual soiling

2=moderate residual soiling

3=considerable residual soiling

4=very considerable residual soiling

5=no cleaning effect

In order to obtain a better differentiation of the cleaning effect, the assessment was made by those carrying it out in steps of 0.5.

Example Formulations:

The formulations listed in tables 1 to 5 below were prepared, the suitability of the barrier-forming components having been ascertained beforehand via the determination of the nephelometric turbidity value (NTU value). The NTU value can be found in table 6. The skin protectants according to the invention are then prepared by stirring together the components specified in the tables by means of the customary methods known in cosmetics.

TABLE 1

Formulations

| Ingredients (INCI names) in % by weight | Form. 1 | Form. 2 | Form. 3 | Form. 4 | Form. 5 |
|---|---|---|---|---|---|
| Ethylhexyl Stearate | 4.00 | 4.00 | 4.00 | 4.00 | 4.00 |
| Glyceryl Stearate SE | 3.50 | 3.50 | 3.50 | 3.50 | 3.50 |
| Glycerin | 3.00 | 3.00 | 3.00 | 3.00 | 3.00 |
| Cetearyl Alcohol | 2.50 | 2.50 | 2.50 | 2.50 | 2.50 |
| Sodium Bischlorophenyl Sulfamine | 2.10 | 2.10 | 2.10 | 2.10 | 2.10 |
| Isopropyl Palmitate | 2.00 | 2.00 | 2.00 | 2.00 | 2.00 |
| Glycol Distearate | 2.00 | 2.00 | 2.00 | 2.00 | 2.00 |
| Biosaccharide Gum-4[1)] | 5.00 | 2.00 | — | — | — |
| Chondrus crispus (carrageenan)[2)] | — | — | 2.00 | — | — |
| Polyurethane-32[3)] | — | — | — | 1.00 | — |
| Sodium Alginate[4)] | — | — | — | — | 2.00 |
| Ceteareth-6 | 1.20 | 1.20 | 1.20 | 1.20 | 1.20 |
| Ceteareth-25 | 0.30 | 0.30 | 0.30 | 0.30 | 0.30 |
| Phenoxyethanol | 0.72 | 0.72 | 0.72 | 0.72 | 0.72 |
| Methylparaben | 0.20 | 0.20 | 0.20 | 0.20 | 0.20 |
| Ethylparaben | 0.02 | 0.02 | 0.02 | 0.02 | 0.02 |
| Propylparaben | 0.02 | 0.02 | 0.02 | 0.02 | 0.02 |
| Butylparaben | 0.02 | 0.02 | 0.02 | 0.02 | 0.02 |
| Isobutylparaben | 0.02 | 0.02 | 0.02 | 0.02 | 0.02 |
| Parfum | 0.20 | 0.20 | 0.20 | 0.20 | 0.20 |
| Aqua | ad 100 | ad 100 | ad 100 | ad 100 | ad 100 |

| Ingredients (INCI names) in % by weight | Form. 6 | Form. 7 | Form. 8 |
|---|---|---|---|
| Ethylhexyl Stearate | 4.00 | 4.00 | 4.00 |
| Glyceryl Stearate SE | 3.50 | 3.50 | 3.50 |
| Glycerin | 3.00 | 3.00 | 3.00 |
| Cetearyl Alcohol | 2.50 | 2.50 | 2.50 |
| Sodium Bischlorophenyl Sulfamine | 2.10 | 2.10 | 2.10 |
| Isopropyl Palmitate | 2.00 | 2.00 | 2.00 |
| Glycol Distearate | 2.00 | 2.00 | 2.00 |
| Hydrolyzed Sclerotium Gum[5)] | 2.00 | — | — |
| Polyglutamic acid[6)] | — | 2.00 | — |
| Polyvinyl alcohol[7)] | — | — | 2.00 |
| Ceteareth-6 | 1.20 | 1.20 | 1.20 |
| Ceteareth-25 | 0.30 | 0.30 | 0.30 |
| Phenoxyethanol | 0.72 | 0.72 | 0.72 |
| Methylparaben | 0.20 | 0.20 | 0.20 |
| Ethylparaben | 0.02 | 0.02 | 0.02 |
| Propylparaben | 0.02 | 0.02 | 0.02 |
| Butylparaben | 0.02 | 0.02 | 0.02 |
| Isobutylparaben | 0.02 | 0.02 | 0.02 |

TABLE 1-continued

| Formulations | | | |
|---|---|---|---|
| Parfum | 0.20 | 0.20 | 0.20 |
| Aqua | ad 100 | ad 100 | ad 100 |

[1] Glycofilm ® 1.5P from Solabia (ca. 1.5% strength solution)
[2] Viscarin ® PC209 Carrageenan from FMC Biopolymer, Philadelphia (USA) or FMC Europe, Brussels (Belgium)
[3] Baycusan ® C1003 from Bayer MaterialScience AG, Leverkusen (Germany)
[4] Kelcosol ® from ISP
[5] Tego Cosmo LSG from Evonik Goldschmidt, Essen
[6] Tego Cosmo PGA from Evonik Goldschmidt, Essen
[7] Mowiol 4-88 from Clariant
[8] Viscarin 389 from FMC Biopolymer
[9] Rewoteric AM C from Evonik Goldschmidt (40% strength solution)
[10] Plantacare ACG 35 = Plantapon ACG LC from Cognis (35% strength solution)
[11] Rewoteric AM KSF 40 from Evonik Goldschmidt (40% strength solution)
[12] Rapithix A60 from ISP
[13] Rewopol SB FA 30 B from Evonik Goldschmidt (33% strength solution)
[14] Rapithix A100 from ISP
[15] Baycusan C1000 from Bayer MaterialScience AG, Leverkusen (Germany)
[16] Hostapon SCI from Clariant (85% strength)
[17] Tegocel HPM 50 from Evonik Goldschmidt, Essen

TABLE 2

| Ingredients (INCI names) in % by weight | Form. 9 | Form. 10 | Form. 11 | Form. 12 | Form. 13 |
|---|---|---|---|---|---|
| Ethylhexyl Stearate | 4.00 | 4.00 | 4.00 | 4.00 | 4.00 |
| Glyceryl Stearate SE | 3.50 | 3.50 | 3.50 | 3.50 | 3.50 |
| Glycerin | 3.00 | 3.00 | 3.00 | 3.00 | 3.00 |
| Cetearyl Alcohol | 1.75 | 1.75 | 1.75 | 1.75 | 1.75 |
| Sodium Bischlorophenyl Sulfamine | 2.00 | 2.00 | 2.00 | 2.00 | 2.00 |
| Isopropyl Palmitate | 2.00 | 2.00 | 2.00 | 2.00 | 2.00 |
| Glycol Distearate | 2.00 | 2.00 | 2.00 | 2.00 | 2.00 |
| Biosaccharide Gum-4 [1] | 5.00 | 2.00 | — | — | — |
| Chondrus crispus [2] | — | — | 0.25 | — | — |
| Polyurethane-32 [3] | — | — | — | 0.25 | — |
| Sodium Alginate [4] | — | — | — | — | 0.25 |
| Ceteareth-6 | 1.20 | 1.20 | 1.20 | 1.20 | 1.20 |
| Ceteareth-25 | 0.30 | 0.30 | 0.30 | 0.30 | 0.30 |
| Phenoxyethanol | 0.72 | 0.72 | 0.72 | 0.72 | 0.72 |
| Methylparaben | 0.20 | 0.20 | 0.20 | 0.20 | 0.20 |
| Ethylparaben | 0.02 | 0.02 | 0.02 | 0.02 | 0.02 |
| Propylparaben | 0.02 | 0.02 | 0.02 | 0.02 | 0.02 |
| Butylparaben | 0.02 | 0.02 | 0.02 | 0.02 | 0.02 |
| Isobutylparaben | 0.02 | 0.02 | 0.02 | 0.02 | 0.02 |
| Parfum | 0.20 | 0.20 | 0.20 | 0.20 | 0.20 |
| Aqua | ad 100 | ad 100 | ad 100 | ad 100 | ad 100 |

TABLE 3

| Ingredients (INCI names) in % by weight | Form. 14 | Form. 15 | Form. 16 | Form. 17 | Form. 18 |
|---|---|---|---|---|---|
| Ethylhexyl Stearate | 4.00 | 4.00 | 4.00 | 4.00 | 4.00 |
| Glyceryl Stearate SE | 3.50 | 3.50 | 3.50 | 3.50 | 3.50 |
| Glycerin | 3.00 | 3.00 | 3.00 | 3.00 | 3.00 |
| Cetearyl Alcohol | 0.500 | 1.75 | 1.75 | 1.75 | 1.75 |
| Sodium Bischlorophenyl Sulfamine | 2.00 | 2.00 | 2.00 | 2.00 | 2.00 |
| Isopropyl Palmitate | 2.00 | 2.00 | 2.00 | 2.00 | 2.00 |
| Sodium Stearoyl Glutamate | 1.44 | 1.44 | 1.44 | 1.44 | 1.44 |
| Cetearyl Alcohol | 0.50 | 0.50 | 0.50 | 0.50 | 0.50 |
| Biosaccharide Gum-4 [1] | 5.00 | 1.00 | — | — | — |
| Chondrus crispus [2] | — | — | 0.25 | — | — |
| Polyurethane-32 [3] | — | — | — | 0.25 | — |
| Sodium Alginate [4] | — | — | — | — | 0.25 |
| Phenoxyethanol | 0.72 | 0.72 | 0.72 | 0.72 | 0.72 |
| Methylparaben | 0.20 | 0.20 | 0.20 | 0.20 | 0.20 |
| Ethylparaben | 0.02 | 0.02 | 0.02 | 0.02 | 0.02 |
| Propylparaben | 0.02 | 0.02 | 0.02 | 0.02 | 0.02 |
| Butylparaben | 0.02 | 0.02 | 0.02 | 0.02 | 0.02 |
| Isobutylparaben | 0.02 | 0.02 | 0.02 | 0.02 | 0.02 |
| Parfum | 0.20 | 0.20 | 0.20 | 0.20 | 0.20 |
| Sodium Chloride | 0.03 | 0.03 | 0.03 | 0.03 | 0.03 |
| Aqua | ad 100 | ad 100 | ad 100 | ad 100 | ad 100 |

| Ingredients (INCI names) in % by weight | Form. 19 | Form. 20 |
|---|---|---|
| Ceteareth-25 | 1.50 | 1.50 |
| Polyglyceryl-3 Methylglucose Distearate | 3.50 | 3.50 |
| Cetylstearyl alcohol | 0.50 | 0.50 |
| Isopropyl palmitate | 2.00 | 2.00 |
| Isooctyl stearate | 4.00 | 4.00 |
| Glycerin | 3.00 | 3.00 |
| Disodium Laureth Sulfosuccinate [13] | | 8.00 |
| Sodium benzoate | 0.60 | 0.60 |
| Lactic acid 80% strength | 0.30 | 0.30 |
| Zinc salicylate | 1.00 | 1.00 |
| Gingko | 0.10 | 0.10 |
| Xanthan Gum | 0.25 | 0.25 |
| Biosaccharide Gum-4 [1] | 2.00 | 2.00 |
| Aqua | ad 100 | ad 100 |

TABLE 4

| Ingredients (INCI names) in % by weight | Form. 21 | Form. 22 | Form. 23 | Form. 24 | Form. 25 | Form. 26 |
|---|---|---|---|---|---|---|
| Ethylhexyl Stearate | 4.00 | 4.00 | 4.00 | 4.00 | 4.00 | 4.00 |
| Glyceryl Stearate SE | 3.50 | 3.50 | 3.50 | 3.50 | 3.50 | 3.50 |
| Glycerin | 3.00 | 3.50 | 3.50 | 3.50 | 3.50 | 3.50 |
| Cetearyl Alcohol | 0.50 | 0.50 | 0.50 | 0.50 | 0.50 | 0.50 |
| Isopropyl Palmitate | 2.00 | 2.00 | 2.00 | 2.00 | 2.00 | 2.00 |
| Biosaccharide Gum-4 [1] | 5.00 | 2.00 | — | — | — | — |
| Chondrus crispus [2] | — | — | 2.00 | — | — | — |
| Polyurethane-32 [3] | — | — | — | 1.00 | — | — |
| Sodium Alginate [4] | — | — | — | — | 2.00 | — |
| Carrageenan [8] | — | — | — | — | — | 2.00 |
| Ceteareth-6 | 1.20 | 1.20 | 1.20 | 1.20 | 1.20 | 1.20 |
| Ceteareth-25 | 0.30 | 0.30 | 0.30 | 0.30 | 0.30 | 0.30 |
| Sodium Cocoamphoacetate [9] | 8.00 | 8.00 | 8.00 | 8.00 | 8.00 | 8.00 |
| Disodium Cocoyl Glutamate [10] | — | — | — | — | — | — |
| Sodium Cocoamphopropionate [11] | — | — | — | — | — | — |
| Phenoxyethanol | 0.72 | 0.72 | 0.72 | 0.72 | 0.72 | 0.72 |

TABLE 4-continued

| | Formulations | | | | | |
|---|---|---|---|---|---|---|
| Methylparaben | 0.20 | 0.20 | 0.20 | 0.20 | 0.20 | 0.20 |
| Ethylparaben | 0.02 | 0.02 | 0.02 | 0.02 | 0.02 | 0.02 |
| Propylparaben | 0.02 | 0.02 | 0.02 | 0.02 | 0.02 | 0.02 |
| Butylparaben | 0.02 | 0.02 | 0.02 | 0.02 | 0.02 | 0.02 |
| Isobutylparaben | 0.02 | 0.02 | 0.02 | 0.02 | 0.02 | 0.02 |
| Parfum | 0.20 | 0.20 | 0.20 | 0.20 | 0.20 | 0.20 |
| Aqua | ad 100 | ad 100 | ad 100 | ad 100 | ad 100 | ad 100 |

| Ingredients (INCI names) in % by weight | Form. 27 | Form. 28 | Form. 29 | Form. 30 | Form. 31 | Form. 32 |
|---|---|---|---|---|---|---|
| Ethylhexyl Stearate | 4.00 | 4.00 | 4.00 | 4.00 | 4.00 | 4.00 |
| Glyceryl Stearate SE | 3.50 | 3.50 | 3.50 | 3.50 | 3.50 | 3.50 |
| Glycerin | 3.00 | 3.50 | 3.50 | 3.50 | 3.50 | 3.50 |
| Cetearyl Alcohol | 0.50 | 0.50 | 0.50 | 0.50 | 0.50 | 0.50 |
| Isopropyl Palmitate | 2.00 | 2.00 | 2.00 | 2.00 | 2.00 | 2.00 |
| Biosaccharide Gum-4 [1] | 5.00 | 2.00 | — | — | — | — |
| *Chondrus crispus* [2] | — | — | 2.00 | — | — | — |
| Polyurethane-32 [3] | — | — | — | 1.00 | — | — |
| Sodium Alginate [4] | — | — | — | — | 2.00 | — |
| Carrageenan [8] | — | — | — | — | — | 2.00 |
| Ceteareth-6 | 1.20 | 1.20 | 1.20 | 1.20 | 1.20 | 1.20 |
| Ceteareth-25 | 0.30 | 0.30 | 0.30 | 0.30 | 0.30 | 0.30 |
| Sodium Cocoamphoacetate [9] | — | — | — | — | — | — |
| Disodium Cocoyl Glutamate [10] | 8.00 | 8.00 | 8.00 | 8.00 | 8.00 | 8.00 |
| Sodium Cocoamphopropionate [11] | — | — | — | — | — | — |
| Phenoxyethanol | 0.72 | 0.72 | 0.72 | 0.72 | 0.72 | 0.72 |
| Methylparaben | 0.20 | 0.20 | 0.20 | 0.20 | 0.20 | 0.20 |
| Ethylparaben | 0.02 | 0.02 | 0.02 | 0.02 | 0.02 | 0.02 |
| Propylparaben | 0.02 | 0.02 | 0.02 | 0.02 | 0.02 | 0.02 |
| Butylparaben | 0.02 | 0.02 | 0.02 | 0.02 | 0.02 | 0.02 |
| Isobutylparaben | 0.02 | 0.02 | 0.02 | 0.02 | 0.02 | 0.02 |
| Parfum | 0.20 | 0.20 | 0.20 | 0.20 | 0.20 | 0.20 |
| Aqua | ad 100 | ad 100 | ad 100 | ad 100 | ad 100 | ad 100 |

| Ingredients (INCI names) in % by weight | Form. 33 | Form. 34 | Form. 35 | Form. 36 | Form. 37 | Form. 38 |
|---|---|---|---|---|---|---|
| Ethylhexyl Stearate | 4.00 | 4.00 | 4.00 | 4.00 | 4.00 | 4.00 |
| Glyceryl Stearate SE | 3.50 | 3.50 | 3.50 | 3.50 | 3.50 | 3.50 |
| Glycerin | 3.00 | 3.50 | 3.50 | 3.50 | 3.50 | 3.50 |
| Cetearyl Alcohol | 0.50 | 0.50 | 0.50 | 0.50 | 0.50 | 0.50 |
| Isopropyl Palmitate | 2.00 | 2.00 | 2.00 | 2.00 | 2.00 | 2.00 |
| Biosaccharide Gum-4 [1] | 5.00 | 2.00 | — | — | — | — |
| *Chondrus crispus* [2] | — | — | 2.00 | — | — | — |
| Polyurethane-32 [3] | — | — | — | 1.00 | — | — |
| Sodium Alginate [4] | — | — | — | — | 2.00 | — |
| Carrageenan [8] | — | — | — | — | — | 2.00 |
| Ceteareth-6 | 1.20 | 1.20 | 1.20 | 1.20 | 1.20 | 1.20 |
| Ceteareth-25 | 0.30 | 0.30 | 0.30 | 0.30 | 0.30 | 0.30 |
| Sodium Cocoamphoacetate [9] | — | — | — | — | — | — |
| Disodium Cocoyl Glutamate [10] | — | — | — | — | — | — |
| Sodium Cocoamphopropionate [11] | 12.00 | 12.00 | 12.00 | 12.00 | 12.00 | 12.00 |
| Phenoxyethanol | 0.72 | 0.72 | 0.72 | 0.72 | 0.72 | 0.72 |
| Methylparaben | 0.20 | 0.20 | 0.20 | 0.20 | 0.20 | 0.20 |
| Ethylparaben | 0.02 | 0.02 | 0.02 | 0.02 | 0.02 | 0.02 |
| Propylparaben | 0.02 | 0.02 | 0.02 | 0.02 | 0.02 | 0.02 |
| Butylparaben | 0.02 | 0.02 | 0.02 | 0.02 | 0.02 | 0.02 |
| Isobutylparaben | 0.02 | 0.02 | 0.02 | 0.02 | 0.02 | 0.02 |
| Parfum | 0.20 | 0.20 | 0.20 | 0.20 | 0.20 | 0.20 |
| Aqua | ad 100 | ad 100 | ad 100 | ad 100 | ad 100 | ad 100 |

| Ingredients (INCI names) in % by weight | Form. 39 | Form. 40 | Form. 41 | Form. 42 | Form. 43 |
|---|---|---|---|---|---|
| Glycerin | 3.00 | 3.00 | 3.00 | 3.00 | 3.00 |
| Propylene Glycol | — | — | — | — | — |
| Capric/Caprylic Triglyceride | 2.00 | 2.00 | 2.00 | 2.00 | 2.00 |
| Sodium Polyacrylate | 0.87 | 0.87 | 0.87 | 0.87 | 0.87 |
| Hydrogenated Polydecene | 0.51 | 0.51 | 0.51 | 0.51 | 0.51 |
| Trideceth-6 | 0.09 | 0.09 | 0.09 | 0.09 | 0.09 |
| Biosaccharide Gum-4 [1] | 5.00 | 2.00 | — | — | — |
| *Chondrus crispus* [2] | — | — | 2.00 | — | — |
| Polyurethane-32 [3] | — | — | — | 2.00 | — |
| Sodium Alginate [4] | — | — | — | — | 2.00 |
| Sodium Cocoamphoacetate [9] | 8.00 | 8.00 | 8.00 | 8.00 | 8.00 |
| Disodium Cocoyl Glutamate [10] | — | — | — | — | — |
| Sodium Cocoamphopropionate [11] | — | — | — | — | — |

TABLE 4-continued

| | Formulations | | | | |
|---|---|---|---|---|---|
| Phenoxyethanol | 0.72 | 0.72 | 0.72 | 0.72 | 0.72 |
| Methylparaben | 0.20 | 0.20 | 0.20 | 0.20 | 0.20 |
| Ethylparaben | 0.02 | 0.02 | 0.02 | 0.02 | 0.02 |
| Propylparaben | 0.02 | 0.02 | 0.02 | 0.02 | 0.02 |
| Butylparaben | 0.02 | 0.02 | 0.02 | 0.02 | 0.02 |
| Isobutylparaben | 0.02 | 0.02 | 0.02 | 0.02 | 0.02 |
| Parfum | 0.20 | 0.20 | 0.20 | 0.20 | 0.20 |
| Aqua | ad 100 | ad 100 | ad 100 | ad 100 | ad 100 |

| Ingredients (INCI names) in % by weight | Form. 44 | Form. 45 | Form. 46 | Form. 47 | Form. 48 |
|---|---|---|---|---|---|
| Glycerin | 3.00 | 3.00 | 3.00 | 3.00 | 3.00 |
| Propylene Glycol | — | — | — | — | — |
| Capric/Caprylic Triglyceride | 2.00 | 2.00 | 2.00 | 2.00 | 2.00 |
| Sodium Polyacrylate [12] | 0.87 | 0.87 | 0.87 | 0.87 | 0.87 |
| Hydrogenated Polydecene [12] | 0.51 | 0.51 | 0.51 | 0.51 | 0.51 |
| Trideceth-6 [12] | 0.09 | 0.09 | 0.09 | 0.09 | 0.09 |
| Biosaccaride Gum-4 [1] | 5.00 | 2.00 | — | — | 2.00 |
| Chondrus crispus [2] | — | — | 2.00 | — | — |
| Polyurethane-32 [3] | — | — | — | 2.00 | — |
| Sodium Alginate [4] | — | — | — | — | 2.00 |
| Sodium Cocoamphoacetate [9] | — | — | — | — | — |
| Disodium Laureth Sulfosuccinate [13] | 18.00 | 12.00 | 8.00 | 8.00 | 12.00 |
| Sodium Cocoamphopropionate [11] | — | — | — | — | — |
| Phenoxyethanol | 0.72 | 0.72 | 0.72 | 0.72 | 0.72 |
| Methylparaben | 0.20 | 0.20 | 0.20 | 0.20 | 0.20 |
| Ethylparaben | 0.02 | 0.02 | 0.02 | 0.02 | 0.02 |
| Propylparaben | 0.02 | 0.02 | 0.02 | 0.02 | 0.02 |
| Butylparaben | 0.02 | 0.02 | 0.02 | 0.02 | 0.02 |
| Isobutylparaben | 0.02 | 0.02 | 0.02 | 0.02 | 0.02 |
| Parfum | 0.20 | 0.20 | 0.20 | 0.20 | 0.20 |
| Aqua | ad 100 | ad 100 | ad 100 | ad 100 | ad 100 |

| Ingredients (INCI names) in % by weight | Form. 49 | Form. 50 | Form. 51 | Form. 52 | Form. 53 |
|---|---|---|---|---|---|
| Glycerin | 3.00 | 3.00 | 3.00 | 3.00 | 3.00 |
| Propylene Glycol | — | — | — | — | — |
| Capric/Caprylic Triglyceride | 2.00 | 2.00 | 2.00 | 2.00 | 2.00 |
| Sodium Polyacrylate [12] | 0.87 | 0.87 | 0.87 | 0.87 | 0.87 |
| Hydrogenated Polydecene [12] | 0.51 | 0.51 | 0.51 | 0.51 | 0.51 |
| Trideceth-6 [12] | 0.09 | 0.09 | 0.09 | 0.09 | 0.09 |
| Biosaccaride Gum-4 [1] | 5.00 | 2.00 | — | — | — |
| Chondrus crispus [2] | — | — | 2.00 | — | — |
| Polyurethane-32 [3] | — | — | — | 2.00 | — |
| Sodium Alginate [4] | — | — | — | — | 2.00 |
| Sodium Cocoamphoacetate [9] | — | — | — | — | — |
| Disodium Cocoyl Glutamate [10] | — | — | — | — | — |
| Sodium Cocoamphopropionate [11] | 8.00 | 8.00 | 8.00 | 8.00 | 12.00 |
| Phenoxyethanol | 0.72 | 0.72 | 0.72 | 0.72 | 0.72 |
| Methylparaben | 0.20 | 0.20 | 0.20 | 0.20 | 0.20 |
| Ethylparaben | 0.02 | 0.02 | 0.02 | 0.02 | 0.02 |
| Propylparaben | 0.02 | 0.02 | 0.02 | 0.02 | 0.02 |
| Butylparaben | 0.02 | 0.02 | 0.02 | 0.02 | 0.02 |
| Isobutylparaben | 0.02 | 0.02 | 0.02 | 0.02 | 0.02 |
| Parfum | 0.20 | 0.20 | 0.20 | 0.20 | 0.20 |
| Aqua | ad 100 | ad 100 | ad 100 | ad 100 | ad 100 |

| Ingredients (INCI names) in % by weight | Form. 54 | Form. 55 | Form. 56 | Form. 57 | Form. 58 |
|---|---|---|---|---|---|
| Glycerin | — | — | — | — | — |
| Propylene Glycol | 3.00 | 3.00 | 3.00 | 3.00 | 3.00 |
| Capric/Caprylic Triglyceride | 2.00 | 2.00 | 2.00 | 2.00 | 2.00 |
| Sodium Polyacrylate [12] | 0.87 | 0.87 | 0.87 | 0.87 | 0.87 |
| Hydrogenated Polydecene [12] | 0.51 | 0.51 | 0.51 | 0.51 | 0.51 |
| Trideceth-6 [12] | 0.09 | 0.09 | 0.09 | 0.09 | 0.09 |
| Biosaccaride Gum-4 [1] | 5.00 | 2.00 | — | — | — |
| Chondrus crispus [2] | — | — | 2.00 | — | — |
| Polyurethane-32 [3] | — | — | — | 2.00 | — |
| Sodium Alginate [4] | — | — | — | — | 2.00 |
| Sodium Cocoamphoacetate [9] | — | — | — | — | — |
| Disodium Cocoyl Glutamate [10] | — | — | — | — | — |
| Sodium Cocoamphopropionate [11] | 8.00 | 8.00 | 8.00 | 8.00 | 8.00 |
| Phenoxyethanol | 0.72 | 0.72 | 0.72 | 0.72 | 0.72 |
| Methylparaben | 0.20 | 0.20 | 0.20 | 0.20 | 0.20 |
| Ethylparaben | 0.02 | 0.02 | 0.02 | 0.02 | 0.02 |

TABLE 4-continued

| Ingredients | | | | | |
|---|---|---|---|---|---|
| Propylparaben | 0.02 | 0.02 | 0.02 | 0.02 | 0.02 |
| Butylparaben | 0.02 | 0.02 | 0.02 | 0.02 | 0.02 |
| Isobutylparaben | 0.02 | 0.02 | 0.02 | 0.02 | 0.02 |
| Parfum | 0.20 | 0.20 | 0.20 | 0.20 | 0.20 |
| Aqua | ad 100 | ad 100 | ad 100 | ad 100 | ad 100 |

| Ingredients (INCI names) in % by weight | Form. 59 | Form. 60 | Form. 61 | Form. 62 | Form. 63 |
|---|---|---|---|---|---|
| Trisodium dicarboxymethyl alaninate | 0.01 | 0.01 | 0.01 | 0.01 | 0.01 |
| Phenoxyethanol | 0.94 | 0.94 | 0.94 | 0.94 | 0.94 |
| Propylene glycol | 3.50 | 3.50 | 3.50 | 3.50 | 3.50 |
| Capric/Caprylic Triglyceride | 2.00 | 2.00 | 2.00 | 2.00 | 2.00 |
| Parfum | 0.20 | 0.20 | 0.20 | 0.20 | 0.20 |
| Sodium polyacrylate [14] | 1.00 | — | 1.00 | 1.00 | 1.00 |
| Sodium Alginate [4] | — | 2.00 | — | — | — |
| Biosaccharide Gum-4 [1] | 2.00 | 2.00 | 2.00 | 2.00 | 2.00 |
| Sodium Cocoamphoacetate [9] | 12.00 | — | — | 18.00 | 6.00 |
| Disodium Laureth Sulfosuccinate [13] | — | 12.00 | — | — | — |
| Sodium Cocoamphopropionate [11] | — | — | 12.00 | — | — |
| Aqua | ad 100 | ad 100 | ad 100 | ad 100 | ad 100 |

| Ingredients (INCI names) in % by weight | Form. 64 | Form. 65 |
|---|---|---|
| Cremophor A6 (BASF) | 1.20 | 1.20 |
| Cremophor A25 (BASF) | 0.30 | 0.30 |
| Glyceryl Stearate SE | 3.50 | 3.50 |
| Glycerin | 3.00 | 3.00 |
| Cetylstearyl Alcohol | 2.50 | 2.50 |
| Ethylene glycol distearate | 2.00 | 2.00 |
| Isopropyl Palmitate | 2.00 | 2.00 |
| Isooctylstearate | 4.00 | 4.00 |
| Polyurethane-32 [3] | 2.00 | — |
| Polyurethane-34 [15] | — | 2.00 |
| Phenoxyethanol | 0.72 | 0.72 |
| Methylparaben | 0.20 | 0.20 |
| Ethylparaben | 0.02 | 0.02 |
| Propylparaben | 0.02 | 0.02 |
| Butylparaben | 0.02 | 0.02 |
| Isobutylparaben | 0.02 | 0.02 |
| Parfum | 0.20 | 0.20 |
| Aqua | ad 100 | ad 100 |

| Ingredients (INCI names) in % by weight | Form. 66 | Form. 67 |
|---|---|---|
| Decyl cocoate | 8.00 | 8.00 |
| Ethylhexyl palmitate | 5.00 | 5.00 |
| Cetyl ricinoleate | 2.00 | 2.00 |
| Cetearyl alcohol | 1.00 | 1.00 |
| Vitamin E acetate | 0.50 | 0.50 |
| Sucrose stearate | 2.00 | 2.00 |
| Cetearyl glucoside | 0.50 | 0.50 |
| Hydrolyzed sclerotium gum | 0.20 | 0.20 |
| Propylene glycol | 4.00 | 4.00 |
| Glycerin | 4.00 | 4.00 |
| Panthenol | 0.50 | 0.50 |
| *Chondrus crispus* [2] | 2.00 | 2.00 |
| Disodium Laureth Sulfosuccinate [13] | 8.00 | — |
| Sodium Cocoamphopropionate [11] | — | 12.00 |
| Phenoxyethanol | 0.72 | 0.72 |
| Methylparaben | 0.20 | 0.20 |
| Ethylparaben | 0.02 | 0.02 |
| Propylparaben | 0.02 | 0.02 |
| Butylparaben | 0.02 | 0.02 |
| Isobutylparaben | 0.02 | 0.02 |
| Parfum | 0.20 | 0.20 |
| Aqua | ad 100 | ad 100 |

TABLE 5

Formulations not according to the invention

| Ingredients (INCI names) in % by weight | Form. A | Form. B | Form. C | Form. D |
|---|---|---|---|---|
| Talc | 21.00 | 21.00 | 21.00 | 21.00 |
| Glycerin | 7.00 | 7.00 | 7.00 | 7.00 |
| Silica | 3.00 | 3.00 | 3.00 | 3.00 |
| Glyceryl Stearate | 2.90 | 2.90 | 2.90 | 2.90 |
| Laureth-10 | 2.00 | 2.00 | 2.00 | 2.00 |
| Bentonite | 0.99 | 0.99 | 0.99 | 0.99 |
| Sodium Phosphate | 0.46 | 0.46 | 0.46 | 0.46 |
| Lactic Acid | 0.20 | 0.20 | 0.20 | 0.20 |
| Potassium Sorbate | 0.30 | 0.30 | 0.30 | 0.30 |
| Dioctyl Sodium Sulfosuccinate | 0.02 | 0.02 | 0.02 | 0.02 |
| Silver Chloride | 0.002 | 0.002 | 0.002 | 0.002 |
| Propylene Glycol | 0.002 | 0.002 | 0.002 | 0.002 |
| Titanium Dioxide | 0.003 | 0.003 | 0.003 | 0.003 |
| Sodium Cocoamphoacetate[9] | 8.00 | — | — | — |
| Disodium Cocoyl Glutamate[10] | — | 8.00 | — | — |
| Sodium Cocoamphopropionate[11] | — | — | 8.00 | — |
| Sodium cocoyl isethionate[16] | — | — | — | 9.00 |
| Parfum | 0.20 | 0.20 | 0.20 | 0.20 |
| Aqua | ad 100 | ad 100 | ad 100 | ad 100 |

| Ingredients (INCI names) in % by weight | Form. E |
|---|---|
| Ethylhexyl Stearate | 4.00 |
| Glyceryl Stearate SE | 3.50 |
| Glycerin | 3.00 |
| Cetearyl Alcohol | 2.50 |
| Sodium Bischlorophenyl Sulfamine | 2.10 |
| Isopropyl Palmitate | 2.00 |
| Glycol Distearate | 2.00 |
| Hydroxypropylcellulose[17] | 2.00 |
| Ceteareth-6 | 1.20 |
| Ceteareth-25 | 0.30 |
| Phenoxyethanol | 0.72 |
| Methylparaben | 0.20 |
| Ethylparaben | 0.02 |
| Propylparaben | 0.02 |
| Butylparaben | 0.02 |
| Isobutylparaben | 0.02 |
| Parfum | 0.20 |
| Aqua | ad 100 |

TABLE 6

Nephelometric turbidity value (NTU, Nephelometric Turbidity Unit)

| Sample (INCI names) | 1% strength by weight solution | 2% strength by weight solution | 3% strength by weight solution |
|---|---|---|---|
| Sodium Alginate[4] (Kelcosol ® from ISP) | 90 | 160 | 192 |
| Sodium Alginate (Algogel ® 3020 from Degussa Texturant Systems France SAS) | 72 | 152 | 202 |
| Biosaccharide Gum-4[1] (Glycofilm ® 1.5 P (H₂O 98%) from C.H. Erbslöh KG, Krefeld) | 66 | 112 | —* |
| *Chondrus crispus* (carrageenan)[2] (Viscarin ® PC209 Carrageenan from FMC Biopolymer) | 48 | 84 | 120 |
| Xanthan Gum (Rhodicare S) | 37 | 78 | —* |
| Hydrolyzed Sclerotium Gum[5] Tego Cosmo LSG | 21 | 41 | 92 |
| Sodium Carboxymethylcellulose WALOCEL ® CRT 2000 | 15 | 29 | —* |
| Hydroxypropylcellulose Klucel ® Hydroxypropyl Methylcellulose[17] Tegocel HPM 50 | 10 | 21.0 | —* |
| | 5 | 9 | 14 |
| Polyglutamic acid[6] Tego Cosmo PGA | 4.9 | 9.5 | 14.4 |
| Polyvinyl alcohol[7] Mowiol ® 4-88 (Clariant) | 0.7 | 1.0 | 1.5 |

| Sample | 0.1% strength by weight solution/WS | 1% strength by weight solution/WS |
|---|---|---|
| Polyurethane-34[15] Baycusan ® C 1000 (H₂O: 56%) | 173 | >1000** |
| Polyurethane-32 Baycusan ® C 1003 (H₂O: 48.4%) | 510 | >1000** |
| Sodium polyacrylate[14] Rapithix ® A 100 (H₂O: 0.4%)** | 443 | —* |

*Measurement not possible (air inclusions, excessively high viscosity, water content).
**A measurement value >1000 is outside of the pregiven measuring range of the instrument.

Test Results:

1. Determination of the LDH Activity

Figure 2:
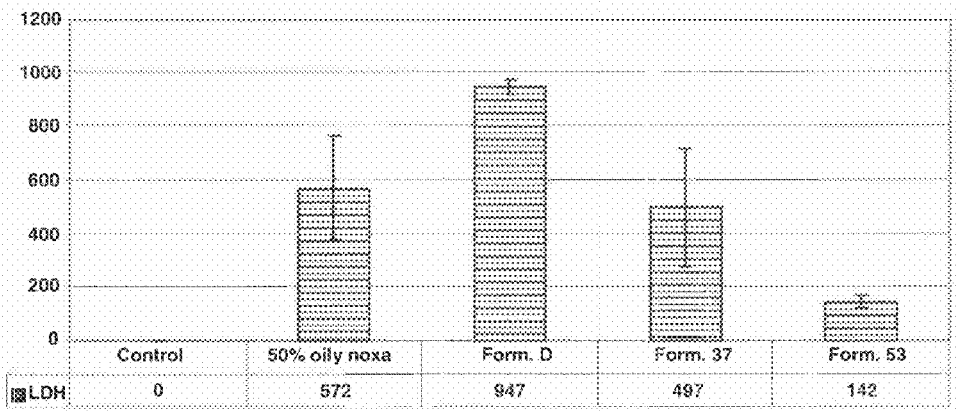
FIG. 2 shows the results of the determination of the LDH activity (3D skin model)

Formulations according to the invention and formulations not according to the invention were applied and then the LDH activity was measured. In a blank sample, the noxae were applied without previously applying a formulation and the LDH activity was determined. The results of the measurements can be found in FIG. 2 and table 7 below.

TABLE 7

Result of the determination of the LDH activity

| | LDH | Standard deviation |
|---|---|---|
| Control | 0 | 0 |
| 50% oily noxae | 572 | 194 |
| Form. D | 947 | 28 |
| Form. 37 | 497 | 221 |
| Form. 53 | 142 | 22 |

Formulations 37 and 53 according to the invention exhibited a considerably reduced amount of released LDH, i.e. these formulations showed a significant protective effect, in contrast to formulation D not according to the invention.

2. Determination of the Cell Viability (Standard MTT Test)

Figure 3:
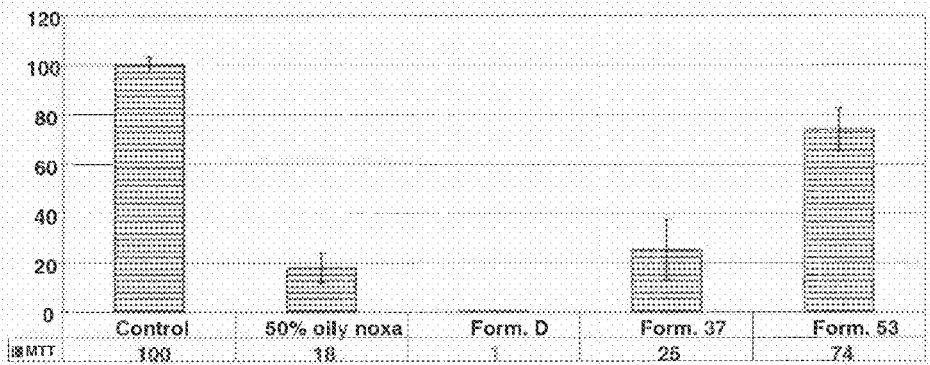
FIG. 3 shows the results of the cell viability (standard MTT test). (3D skin model)

The cell viability was measured for formulations according to the invention and formulations not according to the invention and also a blank sample. The results of the measurements can be found in FIG. 3 and table 8 below.

TABLE 8

Result of the determination of the cell viability

| | MTT | Standard deviation |
|---|---|---|
| Control | 100 | 3.1 |
| 50% oily noxae | 18 | 6.1 |
| Form. D | 1 | 0.1 |
| Form. 37 | 25 | 12.3 |
| Form. 53 | 74 | 8.8 |

Formulations 37 and 53 according to the invention exhibited a considerably increased cell viability, i.e. these formulations displayed a significant protective effect, in contrast to formulation D not according to the invention.

3. Determination of the Interleukin 1α Release

Figure 4:
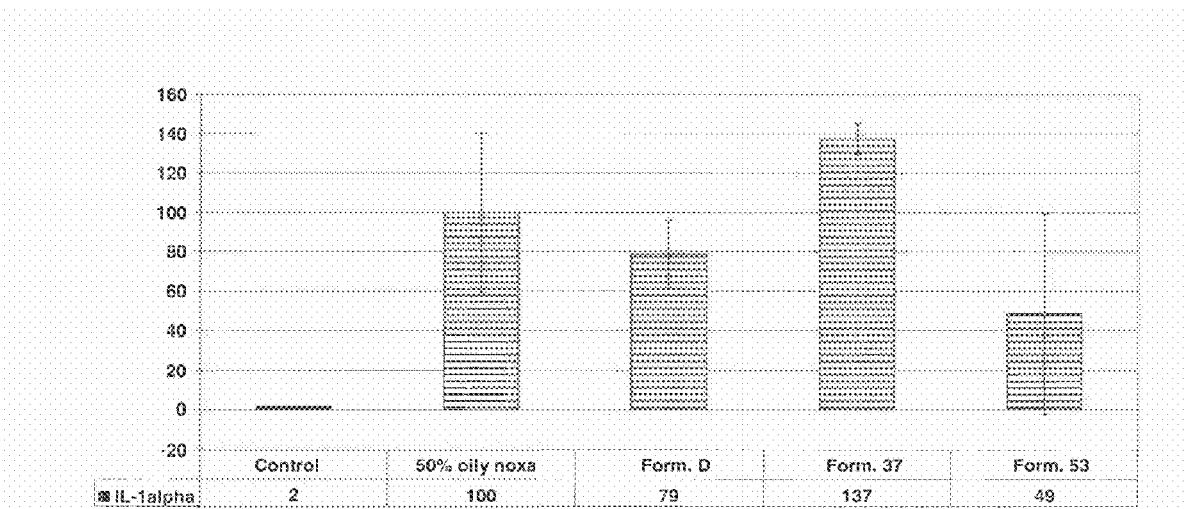
FIG. 4 shows the results of the determination of the interleukin 1α release. (3D skin model)

The interleukin 1α release was determined as described above for formulations according to the invention and formulations not according to the invention and also a blank sample. The results of the measurements can be found in FIG. 4 and table 9 below.

TABLE 9

Result of the determination of the interleukin 1α release

|  | Interleukin 1α | Standard deviation |
| --- | --- | --- |
| Control | 2 | 0.2 |
| 50% oily noxae | 100 | 40.5 |
| Form. D | 79 | 17.4 |
| Form. 37 | 137 | 7.8 |
| Form. 53 | 49 | 50.9 |

Formulation D not according to the invention did not display any inflammatory reaction since the cells had already all died; a regeneration of the skin barrier was no longer possible. Formulation 37 according to the invention exhibited a slight inflammatory reaction, analogous to slight damage. Formulation 53 exhibited, corresponding to the barely present damage, as good as no inflammatory reaction.

4. Determination of Repetitive Occlusive Irritation

Figure 5:
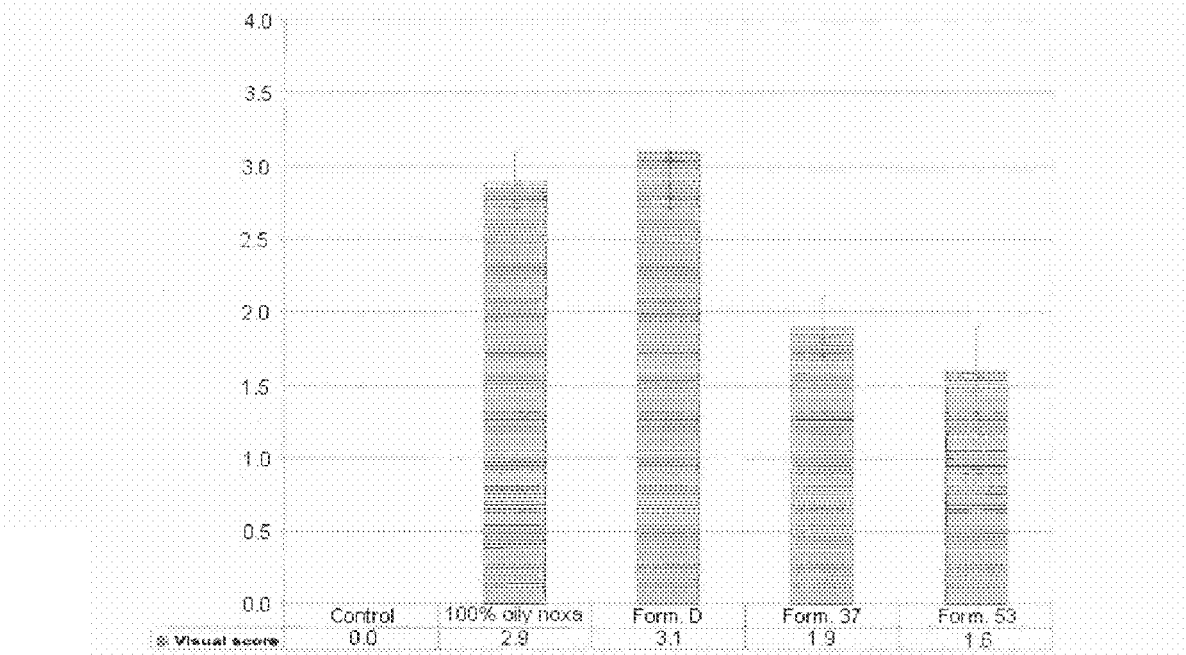
FIG. 5 shows the results of the determination of the repetitive occlusive irritation.

The repetitive occlusive irritation was determined as described above for formulations according to the invention and formulations not according to the invention and also a blank sample. The results of the measurements can be found in FIG. 5 and table 10 below.

TABLE 10

Result of the determination of repetitive occlusive irritation

|  | Visual Score | Standard deviation |
| --- | --- | --- |
| Control | 0.0 | 0.0 |
| 50% oily noxae | 2.9 | 0.2 |
| Form. D | 3.1 | 0.4 |
| Form. 37 | 1.9 | 0.2 |
| Form. 53 | 1.6 | 0.3 |

As table 10 shows, with the formulations according to the invention, considerably lower visual score values were obtained than with formulation D not according to the invention.

Figure 6:
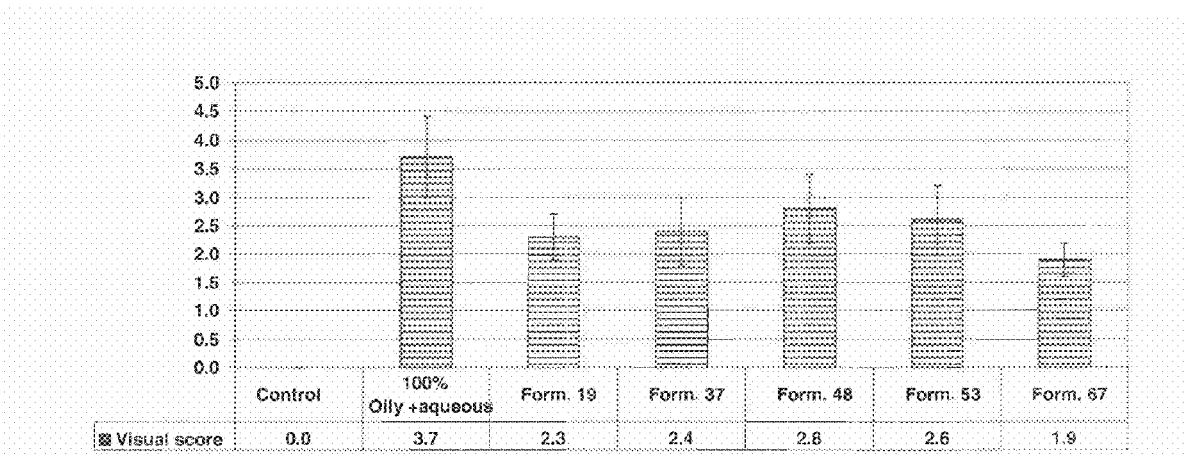
FIG. 6 shows the results of the determination of the repetitive occlusive irritation with change in stress.

For some formulations according to the invention and also a blank sample, repetitive occlusive irritation was determined upon change in stress, as described above. The results of the measurements can be found in FIG. 6 and table 11 below.

TABLE 11

Result of the determination of the repetitive occlusive irritation upon change in stress

|  | Visual Score | Standard deviation |
| --- | --- | --- |
| Control | 0.0 | 0.0 |
| 100% oily noxae + aqueous noxae | 3.7 | 0.7 |
| Form. 19 | 2.3 | 0.4 |
| Form. 37 | 2.4 | 0.6 |
| Form. 48 | 2.8 | 0.6 |
| Form. 53 | 2.6 | 0.6 |
| Form. 67 | 1.9 | 0.3 |

Table 11 shows that by using the skin protectants according to the invention in the event of an alternating effect of oily and aqueous noxae, only slight damage is observed.

5. Handwashing Tests

Figure 7:
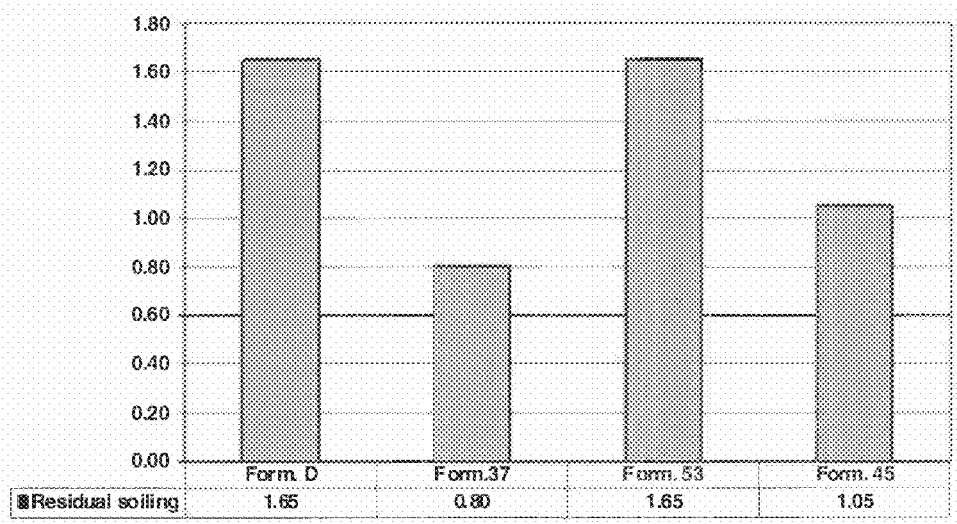
FIG. 7 shows the results of the handwashing test.

Handwashing tests were carried out for formulations according to the invention and formulations not according to the invention and also a blank sample, as described above. The results of the test can be found in FIG. 7 and also table 12 below.

TABLE 12

Results of the handwashing test

|  | Residual soiling |
| --- | --- |
| Form. D | 1.65 |
| Form. 37 | 0.8 |
| Form. 45 | 1.65 |
| Form. 53 | 1.05 |

The handwashing tests show that the skin protectants according to the invention also facilitate and/or promote cleaning of the skin.

The invention claimed is:

1. A skin protectant comprising:
   (a) at least one skin-compatible surfactant,
   (b) at least one polyol that is not etherified,
   (c) at least one component selected from the group consisting of a cosmetic auxiliary, a cosmetic additive, a cosmetic active ingredient, a pharmaceutical auxiliary, a pharmaceutical additive, and a pharmaceutical active ingredient,
   (d) a barrier forming cosmetic component, and
   (e) water,
   wherein the barrier forming component is such that a 1% strength by weight solution of the barrier-forming component in water has a nephelometric turbidity value, determined by turbidimetry, greater than 40 (NTU).

2. The skin protectant of claim 1, wherein the 1% strength by weight solution of the barrier-forming component in water has a nephelometric turbidity value greater than 60.

3. The skin protectant of claim 1, wherein a content of the barrier-forming component in the skin protectant is 0.01 to 5% by weight, based on a total weight of the skin protectant.

4. The skin protectant of claim 1, wherein the barrier-forming component comprises at least one selected from the group consisting of a naturally occurring polymer, and a synthetic polymer.

5. The skin protectant of claim 1, wherein the barrier-forming component comprises at least one selected from the group consisting of a polyurethane, a poly(meth)acrylate, and a polysaccharide.

6. The skin protectant of claim 1, comprising 1 to 12% by weight, based on a total weight of the skin protectant, of said surfactant.

7. The skin protectant of claim 1, comprising 0.1 to 5% by weight, based on the total weight of the skin protectant, of said at least one polyol that is not etherified.

8. The skin protectant of claim 1, comprising 50 to 90% by weight, based on a total weight of the skin protectant, of water.

9. The skin protectant of claim 1, comprising 0.05 to 5% by weight, based on a total weight of composition the skin protectant, of said at least one component selected from the group consisting of the cosmetic auxiliary, the cosmetic additive, the cosmetic active ingredient, the pharmaceutical auxiliary, the pharmaceutical additive, and the pharmaceutical active ingredient.

10. The skin protectant of claim 1, comprising, based on a total weight of the skin protectant, a) from 1 to 12% by weight of the surfactant,
b) from 0.1 to 5% by weight of the polyol that is not etherified,
c) from 0 to 5% by weight of at least one component selected from the group consisting of the cosmetic auxiliary, a cosmetic additive, the cosmetic active ingredient, the pharmaceutical auxiliary, the pharmaceutical additive, and the pharmaceutical active ingredient,
d) from 0.01 to 5% by weight of the barrier-forming component, the 1% strength solution of which in water has a nephelometric turbidity point greater than 40 NTU, and
e) water,
wherein a sum of a) to e) is 100% by weight.

11. The skin protectant of claim 1, wherein the surfactant comprising no fluorine and no silicone.

12. A method to protect skin from hydrophobic and hydrophilic harmful substances, the method comprising:
applying the skin protectant of claim 1 to the skin of a person in need thereof.

13. A method to facilitate skin cleaning, the method comprising: applying the skin protectant of claim 1 to the skin of a person in need thereof.

14. A method for producing the skin protectant of claim 1, the method comprising combining
(a) at least one skin-compatible surfactant,
(b) at least one polyol that is not etherified,
(c) at least one component selected from the group consisting of a cosmetic auxiliary, a cosmetic additive, a cosmetic active ingredient, a pharmaceutical auxiliary, a pharmaceutical additive, and a pharmaceutical active ingredient,
(d) a barrier forming cosmetic component, and
(e) water,
to obtain the skin protectant, wherein the barrier-forming component is such that a 1% by weight strength solution of the barrier forming component in water has a nephelometric turbidity value, determined by turbidimetry, greater than 40 (NTU).

15. The method of claim 14, wherein the skin protectant comprises, based on a total weight of the skin protectant:
from 1 to 12% by weight of (a),
from 0.1 to 5% by weight of (b),
from 0 to 5% by weight of (c), and
from 0.01 to 5% by weight of (d), wherein a sum of (a) to (e) is 100% by weight.

16. The skin protectant of claim 1, wherein a content of the barrier-forming component in the skin protectant is 0.03 to 5% by weight, based on a total weight of the skin protectant.

17. The skin protectant of claim 1, wherein a content of the barrier-forming component in the skin protectant is 0.03 to 3% by weight, based on a total weight of the skin protectant.

18. The skin protectant of claim 1, wherein the barrier forming component comprises at least one polymer selected from the group consisting of gum arabic, carob seed flour, tragacanth, karaya, guar gum, pectin, gellan gum, carrageenan, agar, alginates, *Chondrus crispus*, and biosaccharide gum-4.

19. The skin protectant of claim 1, comprising 1 to 12% by weight, based on a total weight of the skin protectant, of at least one surfactant selected from the group consisting of an amino acid surfactant, an amphoteric surfactant, a zwitterionic surfactant, a polyethylene glycol, and a polypropylene glycol.

* * * * *